United States Patent [19]

Detsch

[11] Patent Number: 4,629,425
[45] Date of Patent: Dec. 16, 1986

[54] DENTAL MIRROR

[76] Inventor: Steven G. Detsch, 4840 Casa Bonita Ct., Bonita, Calif. 92002

[21] Appl. No.: 691,980

[22] Filed: Jan. 16, 1985

[51] Int. Cl.⁴ .............................................. A61C 3/00
[52] U.S. Cl. ...................................... 433/31; 433/29; 433/80
[58] Field of Search ............... 433/31, 29, 80, 81, 433/82, 83, 84, 85, 86; 128/22

[56] References Cited

U.S. PATENT DOCUMENTS

| | | | |
|---|---|---|---|
| 1,989,162 | 1/1935 | Barr | 433/31 |
| 2,176,620 | 10/1939 | Beam | 433/31 |
| 2,720,702 | 10/1955 | Freedman | 433/31 |
| 3,250,005 | 5/1966 | White | 433/30 |
| 3,352,305 | 11/1967 | Freedman | 433/31 |
| 3,614,415 | 10/1971 | Edelman | 433/29 |
| 3,638,013 | 8/1972 | Keller | 433/31 |
| 4,090,506 | 5/1978 | Pilgrim | 128/22 |

FOREIGN PATENT DOCUMENTS 2137584 2/1973 Fed. Rep. of Germany ........ 433/84

Primary Examiner—John J. Wilson
Attorney, Agent, or Firm—Michael W. York

[57] ABSTRACT

Mirror apparatus for examining body cavities such as the mouth including a handle having inner and outer end portions, valve apparatus connected to the outer end portion of the handle and a syringe tip connected to the outer end portion of the valve apparatus. A detachable elongated body cavity member for insertion into a body cavity is provided that can be placed on or removed from the syringe tip as is a detachable mirror assembly that can be placed on or removed from the outer end portion of the body cavity member. The body cavity member has an elongated fiber optic member that can be connected to the end of a flexible fiber optic bundle so that light can be projected onto the mirror surface. The valve apparatus has manual push buttons that permit the delivery of air, water or a spray of air and water to the mirror surface for cleaning the surface. Both the body cavity member and the mirror assembly are made from materials that permit them to be subjected to thermal sterilization.

12 Claims, 10 Drawing Figures

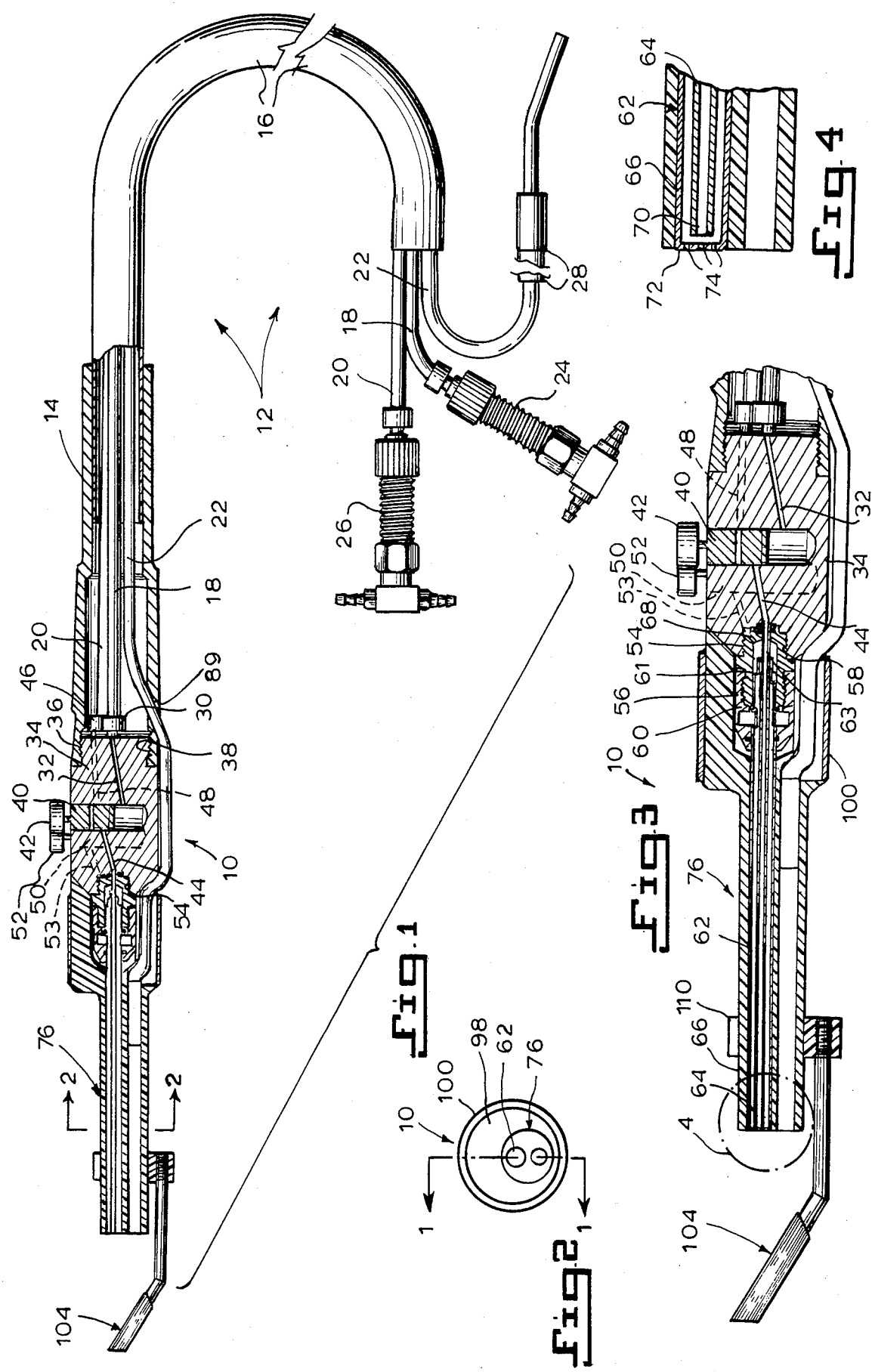

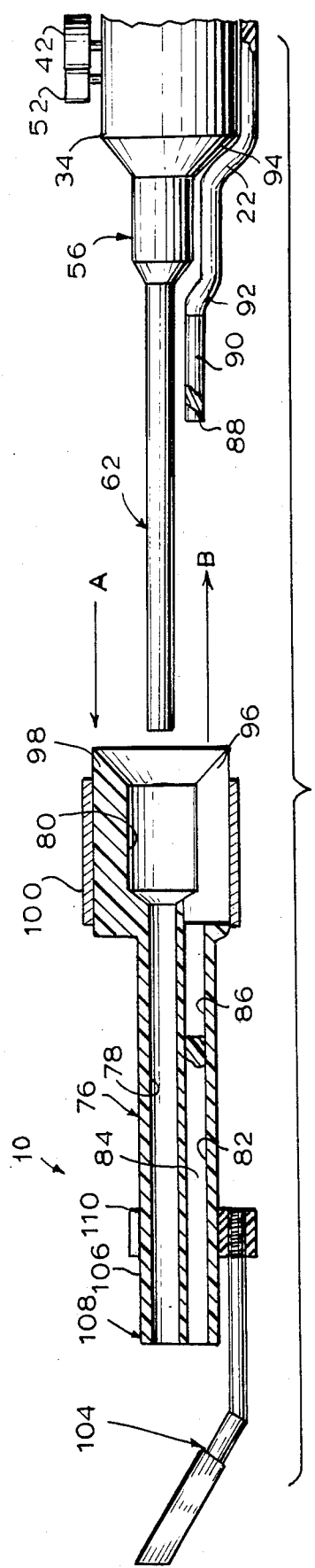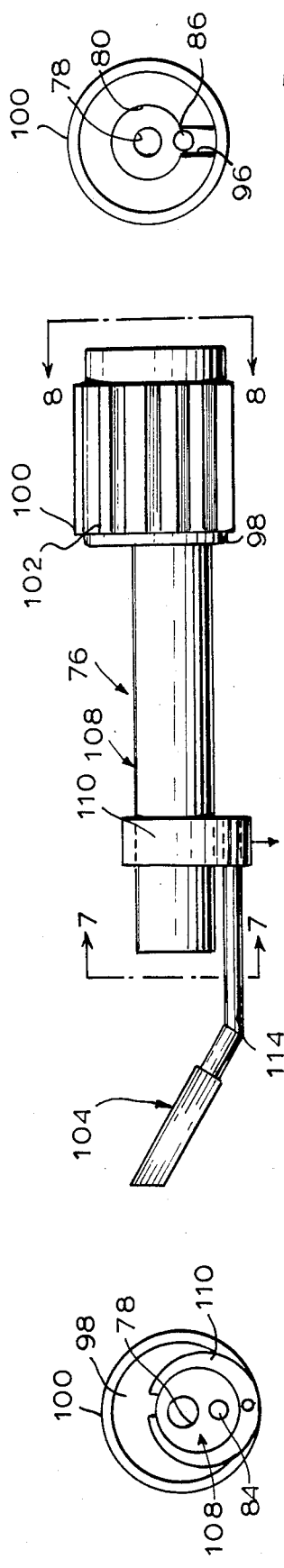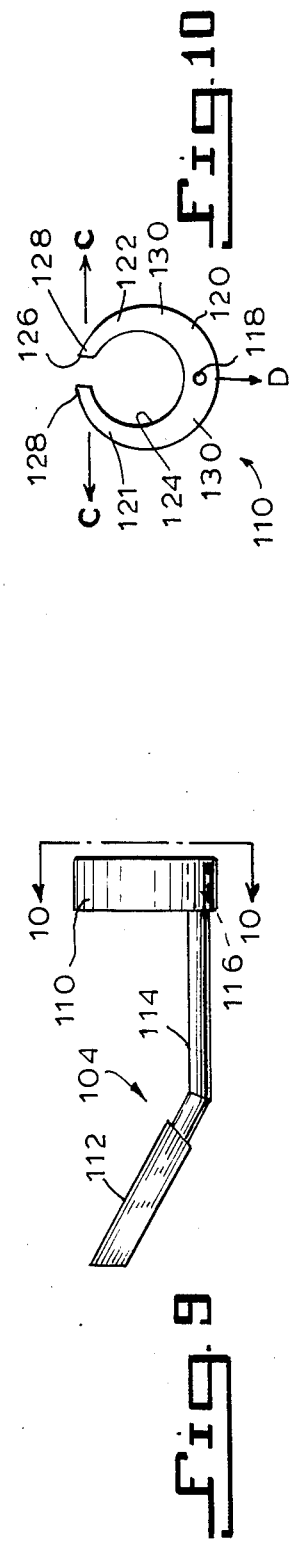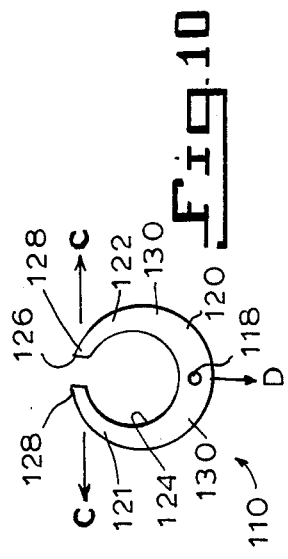

DENTAL MIRROR

BACKGROUND OF THE INVENTION

For many years it has been recognized that it is desirable to illuminate mirrors that are inserted into the mouth or other body cavity to assist the dentist or physician in performing diagnostic or treatment procedures. One such dental mirror is set forth in U.S. Pat. No. 2,176,620. In this patent a dental mirror unit is disclosed that uses a mirror that is illuminated by a light bulb that is in turn connected to a source of electrical power that is external to the dental illuminator unit by means of electrical wires that are connected to a transformer that is in turn connected to a source of conventional house current.

Although such illuminated mirrors had definite advantages and permitted the dentist or physician to obtain a better view of the appropriate portions of the body cavity. The surface of the mirror would frequently become contaminated with aerosols of moisture, frequently mucous or foreign matter such as blood, tooth dust, bone shavings and soft tissue debris resulting from surgical or similar procedures. This contamination would require that the mirror be periodically removed from the mouth or other body cavity and cleaned in order that a proper view could be obtained through the use of the mirror. This cleaning requirement could make diagnostic or thereputic procedures more difficult and greatly increase the time required for such procedures. This is particularly true during dental surgical operations and the like where blood, saliva and tissue remnants would collect on a dry mirror quickly covering the mirror surface requiring that the mirror be removed from the body cavity such as the mouth every thirty seconds (or even more frequently) for cleaning. To make matters worse dried blood and debris on the mirror surface resists removal and hence can cause a significant further delay in the procedure that is being conducted.

A number of dental mirror cleaning devices have been proposed in the past. For instance, U.S. Pat. No. 2,834,109 discloses a dental mirror device that has a bore to permit an air stream to be directed against the mirror surface to permit it to be maintained free of moisture. U.S. Pat. No. 3,092,910 discloses a similar device in which fluid is ejected across the mirror surface. Other U.S. Pat. Nos. 3,118,231; 3,250,005; 3,256,603; 3,342,178 and 3,352,305 disclose the use of water as well as air to clean the mirror surface of a dental mirror device.

Another U.S. Patent discloses the use of fiber optic type systems in connection with a dental mirror type device. U.S. Pat. No. 3,638,013 describes a dental mirror that is used in conjunction with a fiber optic type cable or the like. However, the system disclosed in this patent has no provision for cleaning the mirror surface and apparently requires the use of a separate fiber optic type cable system for its proper operation.

U.S. Pat. No. 4,279,594 discloses a dental hand mirror device that uses fiber optics in conjunction with a mirror. In addition, the dental hand mirror device has provisions for supplying air to the mirror surface to clean it. However, the fiber optic system is used in connection with a two-way mirror and may in practice not be economically practical and effective. In addition, the system is not sterilizable but is disposable and this may compound the possible economic problems associated with this dental mirror device.

This invention overcomes the problems associated with prior art dental mirror devices and the like and permits the mirror surface to be readily illuminated, cleaned, and sterilized. In particular, the invention permits the mirror surface to be exposed to light from a fiber optic system that is to be reflected from the mirror surface. In addition, the mirror surface can be cleaned by air, water or a spray of air and water. The dental mirror device or the like also has an outer portion that is readily removable for cleaning and standard autoclave sterilization. Additionally, the entire device may be readily disconnected from its air, water and light sources and sterilized by ethylene oxide sterilization. The invention may thus be used in the most fastidious hospital operating rooms for illumination and viewing of dental surgical or medical surgical procedures on body cavities.

SUMMARY OF THE INVENTION

This invention relates to dental mirrors and the like and more particularly to dental mirrors or the like that have provisions for both illuminating the mirror and cleaning the mirror surface.

Accordingly, it is an object of the invention to provide an effective dental mirror or the like for use in illuminating a body cavity such as the mouth.

It is an object of the invention to provide a dental mirror or the like that has provisions for readily cleaning the mirror surface.

It is an object of the invention to provide a dental mirror or the like that has provisions for illuminating the mirror surface.

It is an object of the invention to provide a dental mirror or the like that has provisions for cleaning the surface of the mirror without having to remove the mirror from the mouth or other body cavity.

It is an object of the invention to provide a dental mirror or the like that has provisions for substantially simultaneously illuminating the mirror surface with light that is reflected from the mirror surface and cleaning the mirror surface.

It is also an object of the invention to provide a dental mirror or the like that has provisions for illuminating the mirror surface with light that is reflected and provisions for cleaning the mirror surface without removing it from the mouth or other body cavity with a plurality of cleaning media.

It is also an object of the invention to provide a dental mirror or the like that has provisions for illuminating the mirror surface with light that is reflected from the mirror surface and provisions for cleaning the mirror surface without removing the mirror from the mouth or other body cavity with air, water or a spray of water and air.

It is also an object of the invention to provide a dental mirror or the like that has provisions for illuminating the mirror surface with light from a fiber optic system that is reflected from the mirror surface and provisions for cleaning the mirror surface with air, water, or a spray of water and air without removing the mirror from the mouth or other body cavity.

It is also an object of the invention to provide a dental mirror or the like that has provisions for cleaning the surface of the mirror without removing the mirror from the mouth or other body cavity with a plurality of cleaning media and for illuminating the mirror surface with light from a fiber optic system that includes provisions for removing at least a portion of the mirror to permit it to be sterilized.

It is also an object of the invention to provide a dental mirror or the like that has provisions for cleaning the mirror surface without removing the mirror from the mouth or other body cavity and provisions for illuminating the reflecting surface of the mirror with light from a fiber optic system in which the end of the fiber optic system is located at a variable distance from the reflecting surface of the mirror.

It is also an object of the invention to provide a dental mirror or the like that has provisions for cleaning the mirror surface without removing the mirror from the mouth or other body cavity and provisions for illuminating the reflecting surface of the mirror with light from a fiber optic system in which a flexible fiber optic bundle or the like is optically connected to a solid light rod or the like.

The present invention includes mirror apparatus for examining body cavities such as the mouth including a handle member having an inner and outer end portion, a mirror connected to the outer end portion, mirror cleaning means located with respect to the mirror to cause a flow of cleaning media to pass over the reflecting surface of the mirror in which the cleaning means has provisions for supplying three types of cleaning media and fiber optic light means for causing light to be directed to the mirror reflecting surface and to be reflected from the mirror surface.

BRIEF DESCRIPTION OF THE DRAWINGS

The invention will be hereinafter more fully described with reference to the accompanying drawings in which:

FIG. 1 is a side elevational view of the dental mirror apparatus of the invention with a portion thereof illustrated in section to illustrate the interior portions of the invention;

FIG. 2 is a sectional view taken on the line 2—2 of FIG. 1 illustrating by the line 1—1 where substantially the partial sectional view in FIG. 1 is taken;

FIG. 3 is an enlarged view of a portion of the structure illustrated in FIG. 1;

FIG. 4 is an enlarged view of a portion of the structure illustrated in FIG. 3 and taken within the circle 4 thereof;

FIG. 5 is a side elevational view of the structure illustrated in FIG. 3 with a portion thereof in section illustrating how a portion of the invention is removable from another portion;

FIG. 6 is a non-sectional view of a portion of the structure illustrated in FIG. 5;

FIG. 7 is a view of the structure illustrated in FIG. 6 taken substantially on the line 7—7 thereof;

FIG. 8 is a view of the structure illustrated in FIG. 6 taken substantially on the line 8—8 thereof;

FIG. 9 is a side elevational view of a removable portion of the structure illustrated in FIG. 6; and FIG. 10 is an end view of the structure illustrated in FIG. 9 taken substantially on the line 10—10 of FIG. 9.

DETAILED DESCRIPTION OF THE PREFERRED EMBODIMENT

Referring to FIGS. 1, 2, and 3 the dental mirror apparatus of the invention is illustrated and is designated generally by the number 10. In FIG. 1 the sectional portion is taken substantially on the longitudinal center-line of the dental mirror and portions of the attached structure as illustrated in FIG. 2. FIG. 3 is an enlarged portion of the dental mirror apparatus 10 in FIG. 1 and hence the section is also taken substantially on its longitudinal center line. FIG. 1 illustrates a modified conventional air and water system designated generally by the number 12 that is connected to the dental mirror apparatus 10 and forms part of the invention.

The conventional air and water system 12 includes a conventional hose bundle housing 14 that is connected to the dental mirror apparatus 10 in a conventional manner. The bundle housing 14 is connected to and surrounds a conventional hose bundle 16. The hose bundle 16 comprises a hollow flexible tube that surrounds a hollow air line 18 and a hollow water line 20. However, an elongated flexible fiber optic bundle 22 has also been placed inside the hose bundle. The outer end portions of the hollow air line 18 and the water line 20 are connected to quick disconnect valves designated by the respective numbers 24 and 26 that are in turn connectable to respective standard air and water supply systems (not shown). The outer end portion of the fiber optic bundle 22 is connected to a conventional universal fiber optic connector 28.

The inner portion of the hollow air line 18 is connected to a connector 30 that is in turn connected to a conduit 32 in the valve housing 34 that is connected to the end of the hose bundle housing 14 by the threads 36 on the valve housing 34 and the corresponding mating threads 38 on the hose bundle housing 14. The conduit 32 leads to a conventional dental type push button valve designated by the number 40. When this valve 40 is activated by manually pushing its push button 42 downward or toward the valve housing 34 this permits fluid in this case air, to flow from the conduit 32 through the valve 40 to another conduit 44.

In a similar manner, the inner portion of the hollow water line 20 is connected to a connector 46 that is similar to the connector 30 that is in turn connected to a conduit 48 in the valve housing 34 that is similar to the conduit 32. This conduit 48 leads to a conventional dental type push button valve designated by the number 50 that is similar to the valve 40. When this valve 50 is activated by manually pushing its push button 52 downward or toward the valve housing 34 this permits water to flow from the conduit 48 through the valve 50 to a conduit 53 that is similar to the conduit 44 associated with the valve 40.

A threaded circular aperture 54 is located in the forward portion of the valve housing 34. A conventional syringe tip connecting assembly designated by the number 56 has a threaded portion 58 that permits it to be threaded into the threaded aperture 54 in the valve housing 34. The syringe tip connecting assembly 56 has a conventional manually rotatable member 60 that can be rotated to lock or unlock the inner end portion 61 of a conventional syringe tip member 62 in place within the valve housing 34.

When the inner end portion 61 is locked into position in the valve housing 34, water can be fed in a conventional manner to the inner tube 64 of the syringe tip member 62 by the conduit 44 that is in fluid communication with the inner tube 64 of the syringe tip member 62 in view of the aperture 63 in the inner end portion 61 of the syringe tip member 62 when the push button 42 is depressed. Also, when the inner end portion 61 of syringe tip member 62 is locked in place in the valve housing 34, the conduit 53 is in fluid communication with the outer tube 66 of the syringe tip member 62 via the aperture 68 in the inner end portion 61 of the syringe tip member 62 when the push button 52 is depressed.

It is important that the push buttons 42 and 52 be located close together to permit them to be depressed manually by one finger or thumb. In view of this arrangement, that includes the close location of the push buttons 42 and 52, air can be injected into the tube 64 by manually pushing the push button 42 and water can be injected into the tube 66 by manually pushing the push button 52 or both air and water can be injected into the respective tubes or conduits 64 and 66 substantially simultaneously by depressing the push buttons 42 and 52 manually at the same time. This can be accomplished by using one finger or thumb of one hand.

As illustrated in FIG. 4, the exterior portion 70 of the air tube 64 is shorter than the surrounding tube 66 and also the tip or exterior end 72 has a pattern of small holes 74. In view of this arrangement, air can be ejected through these holes 74 from the tube 64 or water can be ejected through these holes 74 from the surrounding tube 66. Also, both water and air can be ejected through the series of holes 74 by manually pushing both of the push buttons 42 and 52 at the same time and this results in a water air spray being ejected through the series of holes 74.

As best illustrated in FIG. 5, the dental mirror apparatus 10 has a manually removable fiber optic end portion designated generally by the number 76. The fiber optic end portion has a length wise aperture 78 that is sized and shaped to receive and slip over the syringe tip member 62. Another larger aperture 80 is located rearwardly of the aperture 78 and substantially concentric therewith that is sized and shaped to receive the exterior of the syringe tip connecting assembly 56. Located below the aperture 78 is another length wise aperture 82 in which the forward portion has a fiber optic core or elongated member 84 securely located in place within the forward portion of the aperture 82 by means known in the art such as by use of a suitable epoxy glue.

Located immediately adjacent and rearwardly of the fiber optic member 84 is a receiving portion 86 of the aperture 82 that is sized and shaped to receive the cylindrical exterior end portion 88 of the optic bundle 22 that exits the hose bundle housing 14 through the aperture 89 (see FIG. 1). The end portion 88 of the optic bundle 22 is surrounded by a thin metal sheath 90 that gives the end portion 88 rigidity to be readily manually inserted into the receiving aperture portion 86 of the removable fiber optic end portion 76. When the end portion 88 is fully inserted into the aperture 86 this provides a light path through the fiber optic bundle 22, the end portion 88 and through the optical member 84.

As indicated in FIG. 5, the removable fiber optic end portion 76 can be manually pulled off the syringe tip member 62 by exerting manual force on the portion or member 76 in the direction of the arrow A that is away from the tip connecting assembly 56 and the associated tip member 62. The removable optic end portion 76 can also be manually pushed on and connected to the tip member 62 by manually pushing it in the direction indicated by the arrow B.

The portion 92 of the optic bundle 22 located adjacent to the end portion 88 is bent or shaped to conform to the exterior of the tip connecting assembly 56 and the forward sloping portion 94 of the valve housing 34. This permits the portion 92 to be slid into the slot 96 in the enlarged substantially cylindrical inner end portion 98 of the removable fiber optic end portion 76.

As indicated in FIGS. 5 and 6, a thin metal ring 100 is located around and secured in a conventional manner to the outside of the enlarged inner end portion 98. The metal ring 100 has elongated projections 102 that project radially outward from the outside surface of the metal ring 100. These projections assist the user in manually rotating the ring 100, the connected inner end portion 98 and the entire manually removable fiber optic end portion to the left or right or clockwise or counterclockwise on the syringe tip member 62 to at least some degree. This permits the mirror assembly designated by the number 104 that is slidably located on the outside surface 106 of the generally cylindrical shaped forward portion 108 of the fiber optic end portion 76 by means of the clip member 110 to also be rotated to the left or right or clockwise or counter clockwise to at least some degree.

FIGS. 6, 7 and 8 illustrate the exterior portions of the fiber optic end portion 76 and associated mirror assembly 104 of FIG. 5 in greater detail. As previously described, the fiber optic end portion 76 has an enlarged substantially cylindrical end portion 98 that is inter connected to the adjacent generally cylindrical shaped forward portion 108. Of course, as best illustrated in FIGS. 6, 7 and 8 the previously described metal ring 100 surrounds the end portion 98. FIG. 8 illustrates the previously mentioned generally rectangular shaped slot 96 and the adjacently located generally circular shaped cross section aperture 86 that is sized and shaped to receive the end portion 88 of the optic bundle 22 that has the metal sheath 90. The substantially concentrically located apertures 78 and 80 that have substantially circular shaped cross sections are also illustrated.

FIGS. 9 and 10 illustrate in further detail the features of the previously described mirror assembly 104. As illustrated the mirror assembly 104 comprises a substantially flat circular shaped mirror 112 that is conventional in nature that is connected at an angle to an elongated substantially cylindrical shaped shaft 114 that has a threaded end portion 116 whose threads are adapted to be threaded into the complimentary threads of an aperture 118 located in the lower portion 120 of the previously mentioned clip member 110. In view of the threaded aperture 118, different types or sizes of mirror assemblies (not shown) can be connected to the clip member 110 by threading their threaded end portions into the aperture 118.

As indicated in FIG. 10, the clip member 110 has two substantially crescent shaped portions 122 that are substantially identical. The inner surface of these portions form substantially a circular surface 124 except that there is a gap or split 126 in the top portion of the clip member 110. It should be noted that the upper portions 128 are thinner than the lower portions 130 of the crescent shaped portions 122 and these features combined with making the clip member 110 from a semi-flexible material permit the upper portions 128 to move outward in the directions indicated by the arrows C in FIG. 10 when a downward force is exerted on the clip member 110 in the direction indicated by the letter D. This permits the clip member 110 and hence the mirror assembly 104 to be removed from the forward cylindrical shaped portion 108 of the fiber optic end portion 76 by exerting a downward force in the direction indicated by the arrow D in FIG. 6.

The dental mirror apparatus 10 is manufactured and used in the following manner. As previously indicated the air and water system designated by the number 12 in FIG. 1 is substantially conventional and similar to those that can be obtained from various sources known to those skilled in the art. However, there are some modifications that include locating the push buttons 42 and 52 closer together in the previously indicated manner than is conventional, locating the elongated fiber optic bundle within the hose bundle 16 and providing an aperture 89 in the hose bundle housing 14. It should also be noted that the push buttons 42 and 52 are offset at a diagonal for ease of thumb or finger placement. Quick disconnect valves 24 and 26 are also connected to the respective ends of the respective air and water lines 18 and 20.

The fiber optic end portion 76 is made from a high temperature plastic type material that is capable of withstanding thermal sterilization by molding in a suitable shaped mold or in the alternative by machining in a manner well known to those skilled in the art or by a combination of these techniques. After the fiber optic end portion 76 is formed, the fiber optic member 84 is secured in place by an epoxy glue or by other suitable known techniques and the metal ring 100 is pressed or crimped in place in a conventional manner. The clip member 110 is formed of the same material and in the same manner as the end portion 76 except that the aperture 118 is threaded in a conventional manner.

The removal and connecting of the optic end portion 76 and the mirror assembly 104 has been previously described and this permits the end portion 76 and the mirror assembly 104 to be readily removed for thermal sterilization between uses. Also as previously indicated, the mirror assembly 104 can be removed individually for thermal sterilization.

Since the mirror 112 and its attached shaft with its threaded end portion 116 can be threaded into or removed from the threaded aperture 118 in the clip member 110, by substituting various size mirrors 112 it is possible to use the invention for viewing a number of body cavities including but not limited to the mouth and larynx.

In using the invention 10 the dentist or physician manually grasps the base bundle assembly member 14 that has the associated attached valve housing 34 and hence the hose bundle assembly forms handle means for manually grasping the mirror apparatus. The user, such as the dentist or physician, then inserts the fiber optic end portion 76 into the appropriate body cavity with or without the attached mirror assembly 104 depending upon the procedures that are to be accomplished. However, usually the mirror assembly is attached and the dentist or physician then can illuminate the mirror 112 through the use of the fiber optic system including the optic member or rod 84 and this permits the user to view at least portions of the cavity in which the optic end portion 76 has been inserted. As the user performs the necessary procedures with the optic end portion 76 and the connected mirror 112 in the body cavity, the mirror can be easily cleaned with air, water or a spray (mixture of air and water) by using a single finger or thumb in the previously described manner. The object to be examined may also be dried by the bouncing air of the mirror onto the surface being observed. This can be accomplished without substantially interrupting the on-going procedures and without removing the mirror 112 and the portion 76 from the body cavity.

Although the invention has been described with reference to a preferred embodiment, it will be understood that variations and modifications may be made within the spirit and scope of the invention as defined in the appended claims

What is claimed is:

1. Mirror apparatus for examining body cavities including a handle member and a mirror having a reflecting surface associated with said handle member wherein the improvement comprises multiple media mirror cleaning means connected to said handle member and located with respect to said mirror for causing a flow of at least three types of mirror reflecting surface cleaning media to pass over the reflecting surface of said mirror for cleaning said mirror reflecting surface, said multiple media cleaning means comprising means for manually selectively causing air, water or a combination of air and water to pass over the reflecting surface of said mirror, and fiber optic light means associated with the handle member of said mirror apparatus for causing light to be directed to said mirror, said fiber optic light means including a flexible fiber optic portion having a portion located in said handle member and a rigid disconnectable fiber optic portion including means for permitting said rigid disconnectable fiber optic portion to be manually disconnected and reconnected to said flexible fiber optic portion, said mirror being removable from and slidably operatively mounted on said disconnectable fiber optic portion.

2. The mirror apparatus of claim 1 wherein said handle member has an outer end portion and said disconnectable fiber optic portion is also disconnectable from the outer end portion of said handle member.

3. The mirror apparatus of claim 2 wherein the outer end portion of said handle member includes a syringe tip member further comprising a fiber optic end portion, wherein said disconnectable fiber optic portion is located within said fiber optic end portion and wherein said fiber optic end portion has a portion thereof sized and shaped to receive at least a portion of said syringe tip member.

4. The mirror apparatus of claim 3 wherein the portion of said fiber optic end portion having a portion thereof sized and shaped to receive at least a portion of said syringe tip member comprises a portion having an aperture for receiving at least a portion of said syringe tip member and wherein said fiber optic end portion is removable from said syringe tip member.

5. The mirror apparatus of claim 4 wherein said fiber optic end portion is rotatable to at least some degree with respect to said syringe tip member.

6. The mirror apparatus of claim 5 further comprising means located on said fiber optic end portion for assisting in manually rotating said fiber optic end portion.

7. The mirror apparatus of claim 5 wherein said fiber optic end portion comprises a material capable of withstanding thermal sterilization.

8. The mirror apparatus of claim 7 wherein said means for permitting said disconnectable fiber optic portion to be manually disconnected and reconnected to said flexible fiber optic portion comprises an aperture in said fiber optic end portion for receiving a portion of said flexible fiber optic portion.

9. The mirror apparatus of claim 8 wherein said means for permitting said disconnectable fiber optic portion to be manually disconnected and reconnected to said flexible fiber optic portion size comprises means located on the adjacent end portion of said flexible fiber optic member for giving said end portion rigidity.

10. The mirror apparatus of claim 9 wherein said multiple media cleaning means includes a hollow flexible air line and a hollow flexible water line and further comprising a hollow flexible tube surrounding said air and said water line and wherein said flexible fiber optic portion has at least a portion thereof located within said hollow flexible tube.

11. The mirror apparatus of claim 10 wherein said hollow flexible air line and said hollow flexible water line each have an outer end portion and further comprising a quick disconnect valve connected to each of said outer end portions.

12. The mirror apparatus of claim 8 further comprising means for operatively connecting different mirror assemblies to said fiber optic end portion.

* * * * *